(12) United States Patent
Lehmann et al.

(10) Patent No.: US 8,033,987 B2
(45) Date of Patent: Oct. 11, 2011

(54) MEDICAL INSTRUMENT

(75) Inventors: Helmut Lehmann, Kraichtal (DE); Markus Lienhart, Ottersweier (DE)

(73) Assignee: Richard Wolf GmbH, Knittlingen (DE)

(*) Notice: Subject to any disclaimer, the term of this patent is extended or adjusted under 35 U.S.C. 154(b) by 1184 days.

(21) Appl. No.: 11/175,934

(22) Filed: Jul. 6, 2005

(65) Prior Publication Data
US 2006/0009677 A1 Jan. 12, 2006

(30) Foreign Application Priority Data
Jul. 6, 2004 (DE) .................. 10 2004 032 523

(51) Int. Cl.
*A61B 1/00* (2006.01)
*G02B 7/02* (2006.01)
(52) U.S. Cl. .................. 600/104; 359/827; 359/903
(58) Field of Classification Search .... 604/164.1–170.3; 600/104; 359/827
See application file for complete search history.

(56) References Cited

U.S. PATENT DOCUMENTS

| | | | | |
|---|---|---|---|---|
| 4,662,197 A | * | 5/1987 | Tietz et al. | 70/276 |
| 5,423,761 A | * | 6/1995 | Hein et al. | 604/167.01 |
| 5,706,143 A | * | 1/1998 | Hipp | 359/824 |
| 6,299,220 B1 | | 10/2001 | Dittrich et al. | |
| 6,641,531 B2 | * | 11/2003 | Kehr | 600/172 |
| 7,229,406 B2 | * | 6/2007 | Kehr et al. | 600/172 |

FOREIGN PATENT DOCUMENTS

| | | |
|---|---|---|
| DE | 197 04 579 | 12/1998 |
| JP | 2000014630 | 1/2000 |
| JP | 2004-22391 | 1/2004 |

OTHER PUBLICATIONS

Search Report dated Sep. 2, 2005, issued for the corresponding British Patent Application No. 0513093.5.
Office Action dated Feb. 1, 2005 in the corresponding German Application No. 10 2004 032 523.5-55.

* cited by examiner

*Primary Examiner* — Theodore Stigell
*Assistant Examiner* — Imani Hayman
(74) *Attorney, Agent, or Firm* — Cozen O'Connor

(57) ABSTRACT

The invention relates to a medical instrument consisting of at least two instrument parts, which is provided with a coupling for releasably connecting the two instrument parts, wherein the coupling having a locking element which may be moved between a released and a locked position, as well as at least one magnet element which produces a magnetic restoring force which retains the locking element in the locked position.

18 Claims, 2 Drawing Sheets

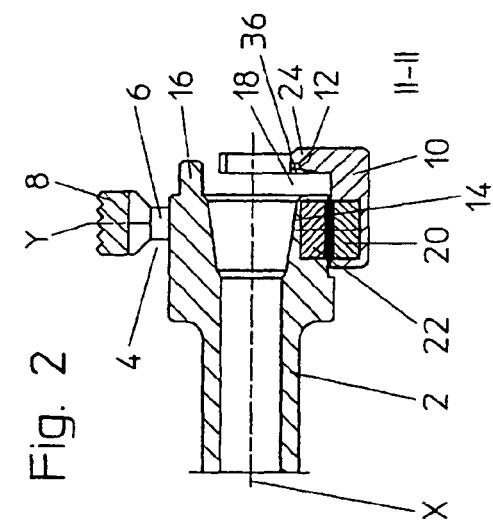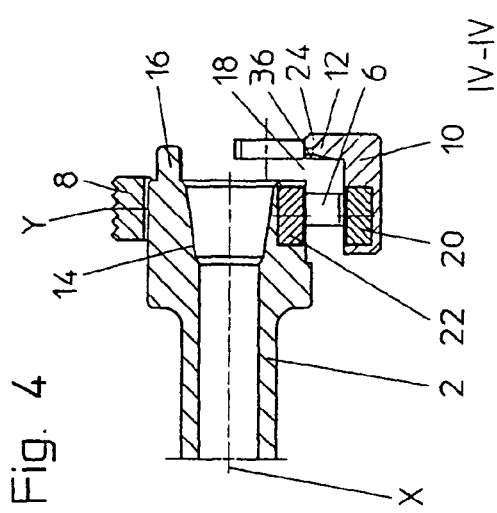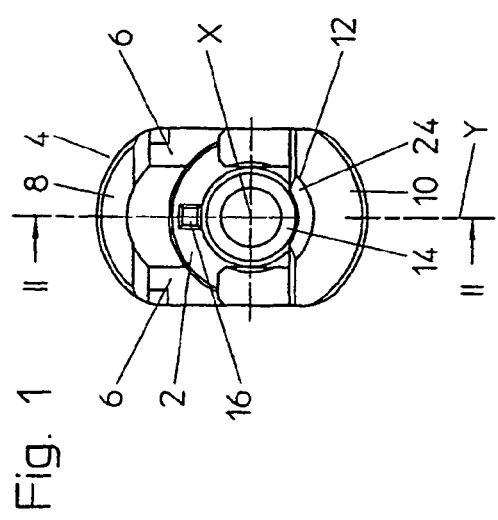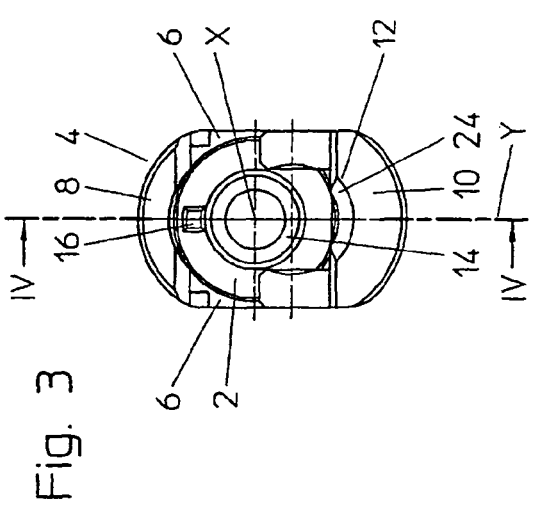

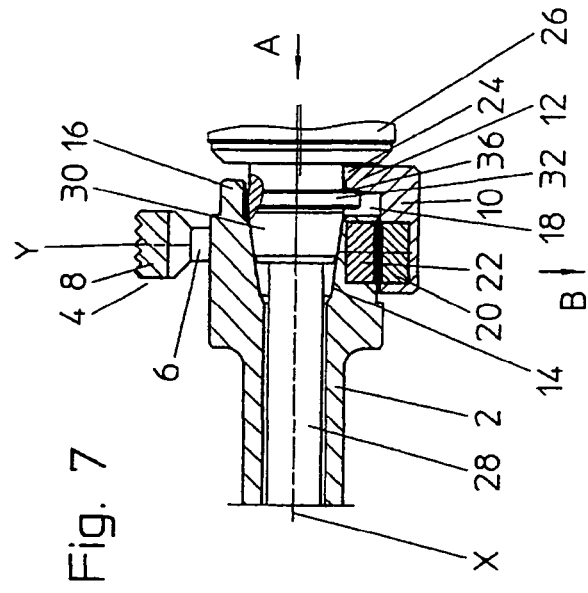
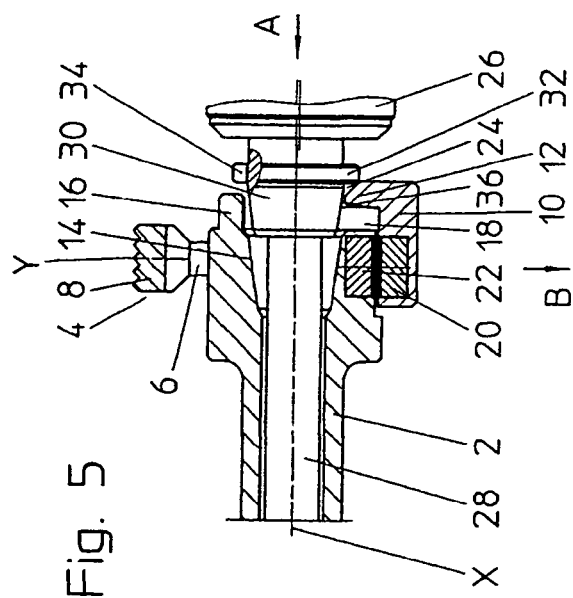
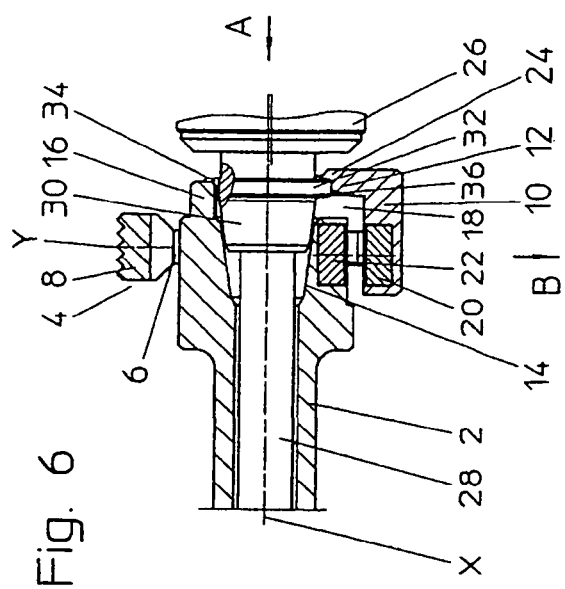

MEDICAL INSTRUMENT

BACKGROUND OF THE INVENTION

1. Field of the Invention

The invention relates to a medical instrument consisting of at least two instrument parts.

2. Description of the Related Art

Such instruments for example are known in the form of endoscopes which comprise a shank into which endoscope optics are applied. For this, the endoscope optics are detachably connected to the proximal end of the shank in the region of their proximal end. Such connections are also present with other endoscopic instruments with which shank-like instrument parts which are inserted in one another may be detachably connected to one another at the proximal end of the instrument. The individual parts must be able to be easily separated from one another in order, for example, during an operation, to be able to exchange instrument parts with other instrument parts, or to be able to also easily dismantle the complete instrument for cleaning.

Such an instrument for example is known from DE 197 04 579 C2. This instrument at the proximal end comprises a coupling for connecting two shank-like medical instruments. The two instruments to be connected comprise bearing surfaces which come to bear on one another in a sealing manner at the interface. Furthermore a box-like slider is provided which engages around the coupling and may be displaced transversely to the connection direction, i.e., to the longitudinal axis of the shank, between a locked and unlocked position. The slider has a keyhole-like receiver and is firmly connected to the one instrument. The keyhole-like receiver may engage behind a bearing shoulder on the other instrument to connect the two instruments to one another. Guide rods and guide springs are arranged in the inside of the box-like slider, which press the slider automatically back into a locked position or move it back into this position.

The disadvantage of this arrangement is the complicated construction of the slider which demands a considerable amount of effort to assemble. Furthermore, the box-like structure with numerous components of the slider which lie at the inside has the disadvantage that this instrument region is very difficult to clean. Contamination in the inside of the slide is very difficult to remove with a standard cleaning of the instrument. Furthermore, the complicated construction often leads to erroneous functions.

SUMMARY OF THE INVENTION

It is therefore the object of the invention to provide an improved medical instrument consisting of at least two instrument parts which comprises a simply constructed, reliably functioning and an easily cleanable coupling between the two instrument parts.

The medical instrument according to the invention has at least two instrument parts, for example, an endoscope shank and endoscope optics to be inserted, and these may be detachably connected to one another via a coupling. The coupling according to the invention comprises a locking element which may be moved between a released and a locked position. This is effected, for example, by way of pressure on the locking element, by which means it may be manually displaced between the two positions. Furthermore, the coupling comprises at least one magnet which produces a magnetic restoring force which acts on the locking element in such a manner that this is held in the locked position and preferably is moved back automatically into the locked position. In contrast to the state of the art, thus, the restoring and locking force acting on the locking element is not produced by spring elements, but by a magnet element, preferably in the form of a permanent magnet.

The arrangement of a magnet element has the advantage that this may be integrated into the components of the coupling in a simple manner. At the same time, the magnet element may be integrated into the components in particular such that it may be arranged flush with the surface of the component accommodating the magnet element. The magnet element may be arranged in the inside of the components which come to bear on one another and are to be magnetically fixed. In this manner, one may avoid undercuts and gaps and interstices which are difficult to clean, which occur, for example, with spring elements. Furthermore, a magnet element permits a more reliable functioning since it permits a force transmission without contact and therefore no jamming or sticking of the elements required for force transmission may occur. Furthermore, the number of required components in the coupling may be reduced, since one may do away with guides and receivers for the spring elements. Thus, the assembly of the instrument is simplified, the reliability is increased, and an instrument is created which is much easier to clean due to the lower number of gaps between the individual components.

To produce a particularly large magnetic retention force or restoring force, one may provide two magnets having an opposite arrangement which attract or repel one another. For example, one magnet element may be provided on the locking element, and a further magnet element on an opposite bearing surface, so that the magnets attract one another and thus move the locking element into the locked position and/or retain it in this position. Alternatively, the magnet elements with their poles may be arranged such that they repel one another and in this manner retain the locking element in the locked position or move it into this position.

Preferably, the locking element is designed as a slider which may be moved in a direction transverse to the connection direction of the two instrument parts between the released and the locked position. The connection direction is that direction in which the two instrument parts are joined onto one another and may be separated from one another. With shank-like instruments such as an endoscope shank with inserted endoscope optics, this is usually the longitudinal axis. Since the locking element is moved in the form of a slider transverse to this connection direction, the release force must likewise be exerted transversely to the connection direction. Thus, one may create a secure connection which may not be inadvertently separated by way of an excess effect of force in the connection direction.

The locking element has an abutment surface which in the locked position comes to bear on an oppositely lying bearing surface on one of the instruments parts. In this manner, the locking element, for example in the form of a slider, has a defined locking position. By way of the contact between the two abutment surfaces one may furthermore produce an audible noise on locking-in, which signalises to the user the correct locking of the instrument.

A magnet element is arranged in the abutment surface on the locking element and/or in the abutment surface on the instrument part. At the same time a magnet element, in particular a permanent magnet, is either arranged only in one of the abutment surfaces, while the other abutment surface is formed by a ferromagnetic material or contains a ferromagnetic element, which is attracted by the magnet element. For producing a greater retention force, one may arrange magnet elements on both bearing surfaces which with regard to their poling are aligned such that they attract one another. In this manner, the bearing surfaces are held firmly to one another. For releasing the locking, accordingly a release force must be exerted which overcomes the magnetic retention force. If the release force is reduced, the locking element by way of the magnetic retention force is moved back again into its locked position. Alternatively, an arrangement is also possible in which the magnet elements are poled such that they repel one another and in this manner retain the locking element in the locked position. With this arrangement, the two magnet elements are separated from one another in the locked position, and to release, the locking element must be moved towards one another against the repulsion force. If this pressure force reduces, the repulsion force between the magnet elements has the effect that these again separate themselves from one another and in this manner move the locking element into the secured position. With this embodiment too, in which the magnet element or the magnet elements are aligned such that two abutment surfaces are attracted to one another, the arrangement may be designed such that the abutment surfaces which are influenced by the magnet force do not bear directly, but further abutments are provided.

Preferably, one of the instrument parts is a tubular shank, and the locking element is arranged at one end of the tubular shank. Such a tubular shank may, for example, be an endoscope shank in which the locking element is arranged at the proximal end. At the proximal end of the endoscopes shank, the locking element permits the connection to working inserts inserted into the endoscope shank, and, in particular, to optics inserted in the endoscope shank.

Preferably, the locking element is guided on the outer side of the shank in a direction normal to the direction of extension of the shank. This guiding permits the actuation of the locking element in a direction normal to the extension direction of the shank and thus, in particular, also normal to the connection direction of the instrument parts.

For this, preferably the locking element comprises two parallel guide limbs which are separated from one another and which, on two diametrically opposed outer sides of the shank, are guided in a linearly movable manner transverse to the extension direction of the shank. In the case of a shank with a round or circular cross-section, the guide limbs are thus guided in the tangential direction to the shank cross-section. The locking element with its guide limbs engages around the shank at two diametrically opposed outer sides. This arrangement of the locking element at the outer side permits easy accessibility and in particular, a simplified cleaning of this instrument region. Since no guide elements and, in particular, restoring elements such as springs need to be arranged in the inside of the locking element, the complete locking element may be designed in an open manner so that it is easy to clean.

The guiding of the guide elements is preferably effected in two parallel grooves extending tangentially on the outer periphery of the shank. Such grooves are simple to form. Furthermore, a very open structure with few undercuts and inaccessible gaps is created, which is easy to clean. For this, the guide limbs preferably lie freely at their outer sides, i.e., are not covered by further guide or retaining elements.

The abutment surface of the locking element is preferably formed on a first connection limb connecting the two guide limbs. This connection limb is preferably designed as a single piece with the guide limb so that the number of the parts to be assembled is reduced. Thus, the guiding of the guide limbs is effected at two sides of the shank which are opposed to one another by 180° and the abutment surface comes to bear on one side of the shank which is offset by 90° to the guides.

A further abutment surface is furthermore preferably formed on the second connection limb lying diametrically opposite the first connection limb between the two guide limbs, which in the released position comes to bear on an oppositely lying abutment surface on the shank. According to this arrangement, the two connection limbs are separated by a distance which is larger than the separation distance of the diametrically opposed abutment surfaces on the shank. For this reason, the abutment surface on the second connection limb is separated from the oppositely lying abutment surface on the shank in the secured position of the locking element. If the locking element is moved into the released position, the abutment surface on the second connection limb comes to bear on the oppositely lying abutment surface on the shank, while simultaneously the bearing surface on the first connection limb is removed from its oppositely lying abutment surface on the shank. The locking element consists of the two guide limbs and the two connection limbs and is thus annular and engages around the shank on its outer periphery, wherein the two straight guide limbs are guided in a linearly movable manner on the outer periphery of the shank. Preferably, one of the connection limbs is detachably connected to the guide limbs, for example via screws, so that the annular structure of the locking element may be opened to assemble this locking element on the shank and, where appropriate, to remove it from the shank again, for example, for repair or maintenance.

The locking element is preferably formed on a first instrument part and comprises an engagement section which, in the locked condition, engages behind an engagement shoulder on the second instrument part. In the case of a tubular instrument part, the engagement shoulder may, for example, be formed as an annular projection or radial projection, e.g., in the form of an annular section, on the outer periphery of the instrument part. For locking, the engagement section by way of displacing the locking element is displaced into the released position such that the engagement shoulder may be moved past the engagement section of the locking element until the engagement section comes into a position behind the engagement shoulder in the connection direction. In this position, the locking element, on account of the magnetic restoring forces, may move back again into its locked position in which the engagement section engages behind the engagement shoulder and firmly holds together the two instrument parts in the connection direction. For release, the locking element is again displaced into the released position, so that the engagement section disengages from the engagement shoulder.

The locking element particularly preferably comprises a contact surface which is inclined to the movement direction of the locking element parts as well as to the connection direction of the two instrument parts, and on assembling the instrument parts comes into contact with an engagement shoulder behind which the locking element is to engage. This chamfer or run-in slope of the locking element has the effect that on contact with the engagement shoulder, the joining force in the connection direction of the instrument parts, on the oblique surface produces a transverse force component which acts in the movement direction of the locking element and may thus automatically displace the locking element into the released condition. On account of the inclined or oblique contact surface, an automatic locking becomes possible on joining together the instrument parts in that the locking element automatically moves into the released condition, and, when the two instrument parts are pushed together far enough in the connection direction, on account of the magnetic restoring forces moves back again into its locked position. In this position, for example, an engagement section of the locking element may engage behind the engagement shoulder on the other instrument part. Thus a very simple handling of the medical instruments is achieved.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

In the drawings:

FIG. 1 a plan view of the proximal end of an endoscope shank with a locking element in its locked position, FIG. 2 a sectioned view of the proximal end of the endoscope shank along the line II-II in FIG. 1, FIG. 3 a view according to FIG. 1 with the locking element in its released position, FIG. 4 a sectioned view along the line IV-IV in FIG. 3, FIG. 5 a sectioned view of the proximal end of the endoscope shank according to FIG. 2 with optics which have not yet been fully inserted, FIG. 6 a view according to FIG. 5 with which the optics are inserted further, and FIG. 7 a view according to FIGS. 5 and 6, with which the optics are completely inserted into the endoscope shank and the locking element is located in the locked position.

DETAILED DESCRIPTION OF THE PRESENTLY PREFERRED EMBODIMENTS

The embodiment example described hereinafter by way of the figures relates to a medical instrument in the form of an endoscope, with an endoscope shank as well as inserted optics. The connection according to the invention of two instrument parts may however also be applied to any other medical instruments, in particular shank-like or tubular medical instruments, with which two instrument parts are to be releasably connected to one another.

First, the coupling part which is formed at the proximal end of the endoscope shank 2 is described by way of FIGS. 1 to 4. At the same time the configuration of the proximal end shown in the FIGS. 1 to 4 may be formed integrally with the endoscope shank or as a separate housing part which is connected to the endoscope shank in a known manner.

FIG. 1 shows a plan view of the proximal end of the endoscope shank 2 in that condition in which the locking element 4 is located in a locked position. The locking element 4 is designed as a slider which encloses the endoscope shank 2 in an annular manner. For this, the locking element 4 comprises two parallel guide limbs 6 which at two diametrically opposed sides of the endoscope shank 2 are guided in two guide grooves which are parallel to one another and which extend tangentially to the outer periphery of the endoscope shank. The guide limbs 6 at their ends are connected to one another in each case by way of connection limbs 8 and 10. At the same time, the connection limb 10 is formed as one piece with the guide limbs 6, while the connection limb 8 is joined to the free ends of the guide limbs 6 and here is connected to this by way of screws. Alternatively, the connection limb 8 may also be connected to the ends of the guide limbs 6 in another suitable manner, e.g., by way of welding. This ensures the assembly ability of the locking element 4 on the endoscope shank 2 in that the locking element 4, with the connection limb 8 removed, is firstly pushed onto the endoscope shank 2, wherein the guide limbs 6 engage into the corresponding guide grooves. In the pushed-on position, the connection limb 8 is then assembled, by which means a closed ring is formed so that the locking element may no longer be removed from the endoscope shank 2, but is held in the guide grooves in a movable manner. The connection limbs 8 and 10 with their inner surfaces which face the endoscope shank 2 form abutment surfaces which limit the degree of movement of the locking element in the direction of the movement axis Y, i.e., normal to the instruments longitudinal axis X.

At the proximal side, an engagement element 12 as one piece with the connection limb 10 is arranged on the locking element 4 and may engage behind an engagement shoulder on the second instrument part for connecting the two instrument parts. The inside of the endoscope shank 2, at the proximal end, is designed as a cone receiver 14 into which the proximal end of the instrument part to be connected may be inserted in a sealing manner. Furthermore, a proximally projecting lug 16 is formed at the proximal end of the endoscope shank 2. The lug is capable of engaging into a corresponding recess on the second instrument part, i.e, the optics, to ensure that the optics are fixed in a predefined angular position with respect to the longitudinal axis X on the endoscope shank 2.

The construction of the locking element 4 may be seen more exactly in the sectional view of FIG. 2. The connection limb 8 at its outer side, i.e., on the side which is distant to the endoscope shank 2, is designed as a press surface which in the shown example is designed in a corrugated (knurled) manner so that it may be securely gripped or pressed to displace the locking element 4 in the direction of the axis Y.

Furthermore, from FIG. 2 it may be seen that the engagement element 12 which is formed on the connection limb 10 is separated a distance from the proximal end-face of the endoscope shank in the proximal direction so that a receiver groove 18 is formed between the engagement element and this end-face, into which an engagement shoulder of the instrument part to be connected may engage.

A permanent magnet 20 is arranged in that inner surface of the connection limb 10 which faces the endoscope shank 2. A second permanent magnet 22 is arranged on the endoscope shank 2 in an oppositely lying bearing surface. The permanent magnets 20 and 22 are applied into recesses of the components which accommodate them. A thin platelet of stainless material, for example stainless steel, in each case is arranged over the permanent magnets 20, 22, which covers the permanent magnets to the outside and closes the recess. The platelets covering the permanent magnets 20 and 22 are connected to the surrounding material in a sealed manner, preferably with a material fit by way of welding or soldering. In this manner the permanent magnets 20 and 22 are completely enclosed in the recesses in a sealed manner, so that they are protected from corrosion, and no gap which is difficult to clean arises. The platelets covering the permanent magnets 20 and 22 are designed in a very thin manner and are preferably applied into the recesses such that their surfaces terminate with the bordering surfaces in a flush manner. A continuous flush surface between the platelets and the surrounding material may be achieved, for example, by way of a common grinding.

Alternatively, the permanent magnets 20 and 22 may in each case be inserted into recesses of the components such that their surfaces terminate with the bordering surfaces in a flush manner and where possible no gaps exist between the permanent magnets 20, 22 and the surrounding material. Possible remaining gaps may be closed with a casting mass, or the permanent magnets 20, 22 are fitted into the recesses with such an over-dimensioning that no gaps at all arise. It is additionally possible for the casting mass to cover the permanent magnets also to the outside, i.e. to the opening of the recess, and thus protect the permanent magnets from corrosion. The flush surfaces may, for example, be achieved by way of grinding after the insertion of the permanent magnets.

The permanent magnets 20 and 22 are arranged lying opposite one another and are poled such that the north pole of the one magnet faces the south pole of the other magnet, so that a maximal attraction force between the permanent magnets 20 and 22 is achieved.

This magnetic attraction force retains the locking element 4 in the position shown in FIGS. 1 and 2 in which the permanent magnets 20 and 22 or the bearing surfaces which surround them bear on one another, and the engagement element 12 has the smallest distance to the longitudinal axis X of the instrument.

An inclined contact surface or run-in slope in the form of a chamfer 24 is formed at the proximal side of the engagement element 12. The chamfer 24 extends obliquely to the instrument longitudinal axis X as well as to the movement axis Y of the locking element 4. When a pressure force is exerted onto the chamfer 24 in the direction of the longitudinal axis X, a force component in the direction of the movement axis Y of the locking element 4 is produced, which is oppositely directed to the magnetic attraction force between the permanent magnets 20 and 22, so that the locking element 4 may move automatically into its unlocked position.

FIG. 3 shows a plan view of the proximal end of the endoscope shank 2 in which the locking element 4 is located in the unlocked position. In this position, which in FIG. 4 is shown once again in section, the connection limb 8 lies on that outer side of the endoscope shank 2 which faces it. Accordingly, the connection limb 10 is distanced to that outer surface of the endoscope shank which lies opposite this limb, i.e., the permanent magnets 20 and 22 are pulled apart and are distanced to one another. By way of this displacement of the locking element 4, the engagement element 12 is distanced further from the longitudinal axis X so that an engagement shoulder may be inserted into the receiver groove 18.

The connection procedure of the endoscope shank 2 to the optics 26 is explained in more detail in FIGS. 5 to 7. The optics 26 comprise an optics shank 28 which is inserted into the endoscope shank 2 from the proximal end. In the region of its proximal end, the optics 26 comprise an optics cone 30 which is inclined corresponding to the cone receiver 14, so that the peripheral surface of the optics cone 30 may come to sealingly bear on the inner surface of the cone receiver 14. An engagement shoulder 32 in the form of a projection is formed on the optics 26 at the proximal side of the optics cone 30, and this shoulder proceeding from the optics shank 28 extends radially outwards. At the same time, the engagement shoulder 32 does not extend radially outwards over the whole periphery. Essentially, the engagement shoulder 32 projects in that region which faces the engagement element 12 of the locking element 4. At the diametrically opposite side, a groove 34 is formed in the engagement shoulder 32, into which the lug 16 may engage in order to position the optics 26 in their angular position with respect to the longitudinal axis X to the endoscope shank 2 in a predefined manner.

If the optics 26 are moved in the connection direction A in the direction of the instrument longitudinal axis X to the proximal end of the endoscope shank 2, first the optics shank 28 is introduced into the inside of the endoscope shank 2. Next, the engagement shoulder 32 with its distal side comes to bear on the chamfer 24. If then the optics 26 continue to be moved in the connection direction A, the chamfer 24 produces a force component which counteracts the attraction force between the permanent magnet 20 and 22 and thus moves the locking element 4 in the direction of the arrow B along the axis Y into its released or unlocked position shown in FIG. 6. In the released position, with a further movement in the connection direction A, the engagement shoulder 32 may be moved past the free end of the engagement element 12 which faces the instrument longitudinal axis X. When the engagement shoulder 32 has passed the engagement element 12, then its gets into the region of the receiver groove 18, and the locking element 4 may move back into its locked position due to the attractive force between the permanent magnets 20 and 22, so that the engagement element 12 engages behind the engagement shoulder 32.

The engagement element 12 is also provided with a chamfer 36 (see also FIG. 4) at the distal side, i.e., the side which is distant to the chamfer 24. This chamfer 36 comes into contact with the proximal side of the engagement shoulder 32 when the engagement shoulder 32 has passed the engagement element 12 on insertion. Due to the attraction force of the permanent magnets 20 and 22, and on account of the chamfer 36, a force component is produced in the direction of the arrow A which presses the optics 26 with the endoscope shank 28 further into the endoscope shank so that the optics cone 30 is pressed against the cone receiver 14 in a firm and sealed manner.

FIG. 7 shows the completely locked position of the locking element 4 in which the permanent magnets 20 and 22 again bear on one another and the optics cone 30 sealingly bears in the cone receiver 14. In order in any case to be able to ensure the sealing bearing of the optics cone 30 and the cone receiver 14, the locking element 4 may be dimensioned such that a distance between the permanent magnets 20 and 22 also remains in the shown locked position, so that a bearing of the optics cone 30 on the cone receiver 14 which is free of play is always achieved via this chamfer 36. The chamfer 36, however, is inclined such that it has an considerably smaller angle to the axis Y, i.e., a larger angle to the longitudinal axis X than the chamfer 24. By way of this, given a tensile force on the optics 26 opposite to the direction A which is too large, the locking element 4 is prevented from being moved automatically into its released position. As a consequence, the locking element 4 is designed such that only on assembly of the endoscope shank 2 and the optics 26 it is automatically moved into its unlocked position and after insertion of the optics is moved back into the locked position, but for releasing the assembled condition it always needs to be manually released by way of pressure on the connection limb 8.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. A medical instrument comprising:
a first element extending along an axis and a second element, the first and second elements being axially, directly and releasably coupled to one another;
a locking element displaceable between a released position and a locking position so that when the locking element is in the locking position the first and second elements are locked together by the locking element and so that when the locking element is in the released position the first and second elements are releasable from one another; and
a magnet element coupled to at least one of the first element and the locking element, the magnet element being operative to produce a magnetic force to urge the locking element into the locking position.

2. The medical instrument of claim 1, wherein the locking element is a slide displaceable transversely to the axis.

3. The medical instrument of claim 1, wherein the first element and the locking element have respective radially opposing peripheral surface segments born against one another when the first and second elements are locked together.

4. The medical instrument of claim 3, wherein the peripheral surface segment of the first element supports the magnet element.

5. The medical instrument of claim 3, wherein the peripheral surface segment of the locking element supports the magnet element.

6. The medical instrument of claim 3, wherein the peripheral surface segments of the first and locking elements support the magnet element.

7. The medical instrument of claim 1, wherein the first element comprises an elongated tubular shank extending between opposite axial ends thereof, the locking element being disposed at one of the axial ends of the shank.

8. The medical instrument of claim 7, wherein the first and locking elements are coupled to one another so that the tubular shank and the locking element are operative to move relative to one another in a plane extending transversely to the axis.

9. The medical instrument of claim 7, wherein the locking element comprises first and second guide limbs radially extending parallel to and spaced apart from one another, the guide limbs being movably mounted on diametrically opposed sides of the shank.

10. The medical instrument of claim 9, wherein the first element has a pair of spaced apart parallel grooves extending tangentially to a periphery of the tubular shank and configured to receive respective first and second guide limbs.

11. The medical instrument of claim 9, wherein the locking element further comprises a first connecting limb peripherally bridging the first and second guide limbs, the first connecting limb and a periphery of the first element having respective surface segments radially opposing one another.

12. The medical instrument of claim 11, wherein the locking element further comprises a second connecting limb spaced diametrically opposite to the first connecting limb and bridging the first and second guide limbs, the second connecting limb and the first element having respective opposing surface segments born against one another in a releasing position of the locking element upon displacing the locking element radially outwards from the locking position.

13. The medical instrument of claim 1, wherein the locking element comprises an engagement section provided with a first locking shoulder, the second element comprising a second shoulder, the first and second shoulders radially extending substantially perpendicular to the axis and overlapping one another in the locking position so that the second shoulder is axially positioned between the first element and the engagement section of the locking element.

14. The medical instrument of claim 13, wherein the first and second shoulders have chamfered surfaces engaging one another in the locking position.

15. The medical instrument of claim 14, wherein the chamfered surfaces of the respective locking and second elements are inclined relative to the axis and relative to a plane extending transversely to the axis, wherein the first and second elements join one another upon engaging the first and second shoulders.

16. The medical instrument of claim 9, wherein the locking element further comprises a first connecting limb peripherally bridging the first and second guide limbs, the first connecting limb and a periphery of the first element having respective surface segments radially opposing one another, the locking element is a slide displaceable transversely to the axis.

17. The medical instrument of claim 9, wherein the locking element further comprises a first connecting limb peripherally bridging the first and second guide limbs, the first connecting limb and a periphery of the first element having respective surface segments radially opposing one another, the respective surface segments being born against one another when the first and second elements are locked together.

18. A medical instrument comprising:
a first element extending along an axis and a second element, the first and second elements being axially, directly and releasably coupled to one another;
a locking element displaceable between a released position and a locking position so that when the locking element is in the locking position the first and second elements are locked together by the locking element and so that when the locking element is in the released position the first and second elements are releasable from one another, the locking element comprising an engagement section which engages behind an engagement shoulder on the second element; and
a magnet element coupled to at least one of the first element and the locking element, the magnet element being operative to produce a magnetic force to urge the locking element into the locking position.

* * * * *